| United States Patent [19] | [11] | 4,260,767 |
| Dusza | [45] | Apr. 7, 1981 |

[54] 2-PYRIDYLHYDRAZIDES

[75] Inventor: John P. Dusza, Nanuet, N.Y.

[73] Assignee: American Cyanamid Company, Stamford, Conn.

[21] Appl. No.: 106,789

[22] Filed: Dec. 26, 1979

[51] Int. Cl.³ .............................................. C07D 213/77
[52] U.S. Cl. .................................... 546/306; 424/263
[58] Field of Search ......................................... 546/306

[56] References Cited

U.S. PATENT DOCUMENTS 3,236,853  2/1966  Schmitt et al. ........................ 546/306

OTHER PUBLICATIONS

Schneller et al., J. Heterocyclic Chem. 1978, vol. 15, pp. 439–444.
Bentley et al., J. Chem. Soc., Perkin II, 1973, pp. 1039–1044.
Jack et al., Chem. Abst. 1972, vol. 70, No. 85819r.

Primary Examiner—Henry R. Jiles
Assistant Examiner—Natalia Harkaway

[57] ABSTRACT

2-Pyridylhydrazides useful as antiinflammatory agents.

7 Claims, No Drawings

2-PYRIDYLHYDRAZIDES

DESCRIPTION OF THE INVENTION

This invention is concerned with all pharmaceutically acceptable 2-pyridylhydrazides having antiinflammatory activity which are new compounds of the general formula:

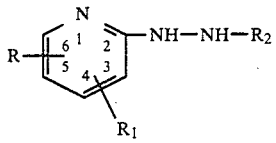

wherein R and $R_1$ are each selected from the group comprising hydrogen and halogen with the proviso that R and $R_1$ cannot both be halogen; $R_2$ is $COCF_3$, $COCH_3$, $COCHF_2$, $COCH_2Cl$, $COCH_2Br$, $COCHCl_2$, $COCHBrCH_3$ and $COOC_2H_5$ and pharmaceutically acceptable salts thereof.

With the preferred embodiment, where R is a chloride at the 6 position, $R_1$ is hydrogen and $R_2$ is $COCH_3$, $COCHF_2$, $COCH_2Cl$, $COCH_2Br$, $COCHCl_2$, $COCHBrCH_3$ and $COOC_2H_5$.

The compounds of the present invention, in general, may be prepared as described in Flow Chart (A).

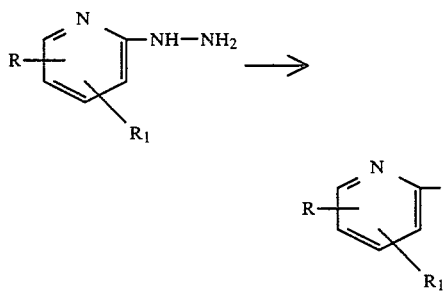

where R, $R_1$ and $R_2$ are as described in the general formula.

The appropriately substituted halo-2-hydrazinopyridine is reacted with the desired carboxylic acid anhydride or carboxylic acid halide in methylene chloride-pyridine at 0°-10° C. for 10 minutes to 2 hours. Evaporation of the solvent and treatment of the solid with aqueous sodium bicarbonate provides the crude product which is recrystallized from a solvent or solvent mixture such as methylene chloride, heptane, chloroform, chloroform-hexane, tetrahydroguran-hexane and the like to provide the appropriate 2-pyridylhydrazide compound of the invention.

The preferred embodiment compounds of the present invention may be prepared as described in Flow Chart (B).

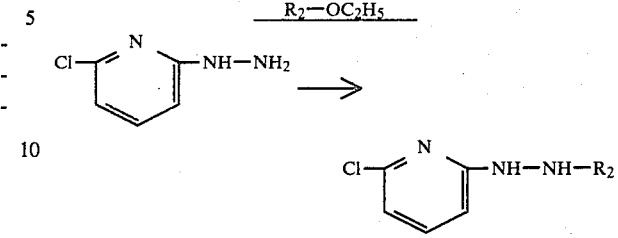

where $R_2$ is as described in the preferred embodiment. The preferred embodiment compounds are prepared as previously described with the exception of an alternative procedure whereby the 6-chloro-2-hydrazinopyridine is heated at reflux with the desired dihaloacetate in a solvent such as ethanol to provide the corresponding hydrazide compound which is recrystallized from a solvent such as chloroform.

Specific compounds included within the scope of this invention are, for example (Chemical Abstract nomenclature given in parentheses):

2-(6-Chloro-2-pyridyl)trifluoroacetic acid, hydrazide (trifluoroacetic acid 2-(6-chloro-2-pyridinyl)hydrazide)

2-(6-Chloro-2-pyridyl)dichloroacetic acid, hydrazide (dichloroacetic acid 2-(6-chloro-2-pyridinyl)hydrazide)

2-(5-Chloro-2-pyridyl)trifluoroacetic acid, hydrazide (trifluoroacetic acid 2-(5-chloro-2-pyridinyl)hydrazide)

2-(6-Bromo-2-pyridyl)trifluoroacetic acid, hydrazide (trifluoroacetic acid 2-(6-bromo-2-pyridinyl)hydrazide)

2-(5-Bromo-2-pyridyl)trifluoroacetic acid, hydrazide (trifluoroacetic acid 2-(5-bromo-2-pyridinyl)hydrazide)

2-(2-Pyridyl)trifluoroacetic acid, hydrazide (trifluoroacetic acid 2-(2-pyridinyl)hydrazide)

2-(6-Chloro-2-pyridyl)acetic acid hydrazide (acetic acid 2-(6-chloro-2-pyridinyl)hydrazide)

3-(6-Chloro-2-pyridyl)carbazic acid, ethyl ester (ethyl 2-(6-chloro-2-pyridinyl)hydrazinecarboxylate)

2-(6-Chloro-2-pyridyl)difluoroacetic acid, hydrazide (difluoroacetic acid 2-(6-chloro-2-pyridinyl)hydrazide)

2-(6-Chloro-2-pyridyl)chloroacetic acid, hydrazide (chloroacetic acid 2-(6-chloro-2-pyridinyl)hydrazide)

2-(6-Chloro-2-pyridyl)-2-bromopropionic acid, hydrazide (2-bromopropanoic acid 2-(6-chloro-2-pyridinyl)hydrazide)

2-(6-Chloro-2-pyridyl)-2-bromoacetic acid, hydrazide (bromoacetic acid 2-(6-chloro-2-pyridinyl)hydrazide)

The novel compounds of the present invention possess valuable properties for meliorating inflammation in mammals.

The following test shows the activity of the compounds of the present invention against chronic inflammation in adjuvant induced arthritis which is accompanied by joint destruction. Groups of three Royal Hart Wistar strain rats, weighing 200±10 g. each were injected intradermally in the right hind paw with Freund's adjuvant (dried human tubercle bacilli in a mineral oil vehicle) at a dose of 2 mg./kg. of body weight. Test compound was administered orally in a 1.5% starch vehicle at the indicated dosage in mg./kg. of body weight once daily on days 0 through 13 post-challenge. Control rats were treated in a similar manner, but given starch vehicle instead of the test compound. On the 14th day post-challenge the diameter of the injected paw (primary lesion) is measured by micrometer caliper. From these measurements of inflamed paws a determination is made of the Relative Surface Area (R.S.A.). This is a ratio expressed as Mean Surface Area of paws of 3 treated rats/Mean Surface area of paws of 60 control rats. If the Relative Surface Area is equal to or less 0.76 the compound is tested again. After the second test the Mean Relative Surface Area (R.S.A.) for the rat paws from both tests is calculated and if the Mean R.S.A. is equal to or less than 0.736 the compound is tested a third time and if the Mean R.S.A. of all 3 tests is less than 0.753 the compound is accepted as active. Compounds found to be active are retested in the same manner to confirm activity. All data is based on use of 18 rats. Table I shows the results of this test conducted with the compounds of the present invention.

TABLE I

| Compound | Dose mg./kg. | Mean R.S.A.* |
|---|---|---|
| 2-(6-Chloro-2-pyridyl)trifluoroacetic acid, hydrazide | 50 | 0.50 |
| 2-(6-Bromo-2-pyridyl)trifluoroacetic acid, hydrazide | 50 | 0.57 |
| 2-(5-Bromo-2-pyridyl)trifluoroacetic acid, hydrazide | 25 | 0.54 |
| 2-(6-Chloro-2-pyridyl)acetic acid hydrazide | 50 | 0.51 |
| 2-(6-Chloro-2-pyridyl)difluoroacetic acid, hydrazide | 50 | 0.42 |
| 2-(6-Chloro-2-pyridyl)-2-bromopropionic acid hydrazide | 50 | 0.64 |
| 2-(6-Chloro-2-pyridyl)-2-bromoacetic acid, hydrazide | 50 | 0.72 |

*Active compounds produce a mean relative rat paw surface area (R.S.A.) of less than 0.753.

In determining the acute antiinflammatory activity of the compounds of the present invention, Royal Hart, Wistar strain rats ranging in weight from 80 to 90 grams were used. The rats were fasted overnight prior to dosing but had free access to water. The compounds were administered in aqueous suspension, by gavage, in a volume of 1.7 ml. per 50 grams of rat [corresponds to hydration volume used by Winter et al., Proc. Soc. Exp. Biol. & Med. 111, 544–547 (1962)]. The phlogistic agent used was carrageenin prepared as a sterile 1% suspension in 0.9% aqueous sodium chloride for routine testing. A volume of 0.05 ml. was injected through a 26 gauge needle into the planter tissue of the right hind paw. Measurements were made 5 hours after drug administration (4 hours after carrageenin challenge). Volumes of both the normal and carrageenin inflamed feet were determined. The difference between the two measurements is considered to be the increased edema due to the carrageenin administration. Results are expressed as a C/T efficacy ratio (edema of control animals/edema of treated animals) and C/T ratio of greater than 1.41 is considered as active. Table II records the results of this test at the indicated dose levels of the compounds of the present invention in comparison with known antiinflammatory agents.

TABLE II

The Effect of Antiinflammatory Agents on Carrageenin Induced Edema of the Rat Paw

| Compound | Dose mg./kg. of body weight | No. of Rats | C/T Edema Ratio |
|---|---|---|---|
| Controls | | 64 | |
| Aspirin | 250 | 32 | 2.8 |
| Phenylbutazone | 250 | 32 | 2.3 |
| Indomethacin | 250 | 32 | 2.9 |
| 2-(6-Chloro-2-pyridyl)trifluoroacetic acid, hydrazide | 125 | 8 | 1.8 |
| 2-(6-Chloro-2-pyridyl)dichloroacetic acid, hydrazide | 250 | 8 | 2.1 |
| (5-Chloro-2-pyridyl)-2-trifluoroacetic acid, hydrazide | 125 | 8 | 2.1 |
| 2-(5-Bromo-2-pyridyl)trifluoroacetic acid, hydrazide | 125 | 8 | 2.2 |
| 2-(2-Pyridyl)trifluoroacetic acid, hydrazide | 125 | 8 | 2.8 |
| 3-(6-Chloro-2-pyridyl)carbazic acid, ethyl ester | 250 | 8 | 1.7 |
| 2-(6-Chloro-2-pyridyl)chloroacetic acid, hydrazide | 250 | 8 | 2.6 |
| 2-(6-Chloro-2-pyridyl)-2-bromoacetic acid, hydrazide | 250 | 4 | 2.7 |

The active components of this invention can be used in compositions such as tablets; the principal active ingredient is mixed with conventional tableting ingredients, such as corn starch, lactose, sucrose, sorbitol, talc, stearic acid, magnesium stearate, dicalcium phosphate, gums or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating.

The liquid forms in which the novel compositions of the present invention may be incorporated for administration include suitably flavored emulsions with edible oils, such as cottonseed oil, sesame oil, coconut oil, peanut oil, and the like. Sterile suspensions or solutions can be prepared for parenteral use.

The term dosage form as described herein refers to physically descrete units suitable as unitary dosage for a warm-blooded animal subject, each unit containing a predetermined quantity of active component calculated to produce the desired therapeutic effect in association with the required pharmaceutical diluent, carrier or vehicle. The dosage may vary from one to 70 mg./kg. of warm-blooded animal per day, preferably in multiple doses. The daily dosage requirement may be from 50 to 2000 mg. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

SPECIFIC DISCLOSURE

The following specific examples illustrate the preparation of the compounds of the present invention.

EXAMPLE 1

2-(6-Chloro-2-pyridyl)trifluoroacetic acid, hydrazide

A solution of 50.0 g. of 2,6-dichloropyridine in 120 ml. of hydrazine hydrate is heated on a steam bath for 6 hours. A product is precipitated upon cooling and the mixture is stored at 4° C. overnight. The mixture is filtered and the colorless crystals obtained are washed once with 100 ml. of ice-cold water and air dried. The product is recrystallized from chloroform-hexane to yield 39.5 g. of 2-chloro-6-hydrazinopyridine.

A mixture of 10.7 g. of the preceding product and 100 ml. of methylene chloride is cooled to 0° C., then a solution of 17.3 g. of trifluoroacetic anhydride in 20 ml. of methylene chloride is added dropwise with stirring. When the addition is complete the reaction mixture is stirred for an additional 10 minutes, then the solvent is evaporated. The resulting colorless solid is treated with a saturated aqueous solution of sodium bicarbonate, then the product is collected, rinsed with cold water and air-dried. The colorless solid is recrystallized from chloroform-hexane to yield 11.4 g. of the product of the Example m.p. 164.5° C.

EXAMPLE 2

2-(6-Chloro-2-pyridyl)dichloroacetic acid, hydrazide

A mixture of 3.0 g. of 2-chloro-6-hydrazinopyridine (prepared in Example 1), 1.8 g. of pyridine and 50 ml. of methylene chloride is cooled to 0° C. in a ice bath, then a solution of 3.23 g. of dichloroacetyl chloride in 10 ml. of methylene chloride is added dropwise with stirring. The reaction mixture is stirred for 2 hours, then the fine precipitate is collected and rinsed with ice-cold methylene chloride and dried to provide 4.0 g. of the product of the Example m.p. 198°–200° C.

EXAMPLE 3

2-(5-Chloro-2-pyridyl)trifluoroacetic acid, hydrazide

A 14.8 g. amount of 2,5-dichloropyridine in 25 ml. of hydrazine hydrate is heated at reflux for 2½ hours. The mixture is cooled, providing crystals. The material is recrystallized from ethyl acetate to yield 9.46 g. of 5-chloro-2-hydrazinopyridine.

A 7.17 g. portion of the preceding product is suspended in 50 ml. of methylene chloride, then 6.6 ml. of trifluoroacetic anhydride is added with stirring to achieve solution. The solution is allowed to stand 1–2 hours with formation of a precipitate. The solvent is removed in vacuo and the resulting solid is treated with 10% aqueous sodium bicarbonate until effervescence ceases. The resulting solid is dissolved in ethyl acetate and passed through magnesium silicate. The filtrate is evaporated on a steam bath with addition of heptane until an oil is formed. The oil is cooled to provide 5.94 g. of the product of the Example as an off-white crystalline solid m.p. 148°–149° C.

EXAMPLE 4

2-(6-Bromo-2-pyridyl)trifluoroacetic acid, hydrazide

A mixture of 20.0 g. of 2,6-dibromopyridine and 50 ml. of hydrazine hydrate is treated by the procedure of Example 1 to yield 11.8 g. of 2-bromo-6-hydrazinopyridine as a colorless solid.

A mixture of 4.0 g. of the preceding product and 50 ml. of methylene chloride is cooled to 0° C. in an ice bath, then a solution of 4.55 g. of trifluoroacetic anhydride in 10 ml. of methylene chloride is added dropwise with stirring. When the addition is complete the mixture is stirred for an additional ½ hour at room temperature then is filtered. The filtrate is treated with a saturated aqueous solution of sodium bicarbonate and is filtered to collect 1.3 g. of colorless solid. This filtrate is treated with additional sodium bicarbonate solution then is extracted 3 times with chloroform and twice with ethyl acetate. The combined chloroform extracts are evaporated to yield 1.0 g. of solid and the ethyl acetate extracts yield an additional 2.5 g. of crude product. The combined solid (3.8 g.) is recrystallized twice from tetrahydrofuran-hexane to yield 3.1 g. of the product of the Example m.p. 166°–169° C.

EXAMPLE 5

2-(5-Bromo-2-pyridyl)trifluoroacetic acid, hydrazide

A mixture of 10.0 g. of 2,5-dibromopyridine and 20 ml. of hydrazine hydrate is treated by the procedure of Example 1 to yield 5.5 g. of 5-bromo-2-hydrazinopyridine as a colorless solid.

A mixture of 4.0 g. of the above product and 50 ml. of methylene chloride is treated with 4.55 g. of trifluoroacetic anhydride in 10 ml. of methylene chloride as described in Example 4. The resulting clear yellow solution is treated with saturated sodium bicarbonate solution and extracted with chloroform, then with ethyl acetate. The extracts are combined, passed through magnesium silicate and evaporated to give a light yellow solid. The solid is recrystallized from benzene-hexane to yield 3.8 g. of the product of the Example m.p. 167°–168° C.

EXAMPLE 6

2-(2-Pyridyl)trifluoroacetic acid, hydrazide

A mixture of 5.1 g. of 2-hydrazinopyridine (Aldrich) and 25 ml. of methylene chloride is treated with 12.2 g. of trifluoroacetic anhydride in methylene chloride as described in Example 4. When the addition is complete the mixture is stirred for 20 minutes, then is removed from the cooling bath and stirred at room temperature for 10 minutes. The mixture is evaporated to a white solid. The solid is treated with a saturated aqueous solution of sodium bicarbonate yielding a yellow solution which is extracted with chloroform. The chloroform is evaporated to yield 6.65 g. of crude product. This product is treated with saturated sodium bicarbonate solution and filtered. The filtrate is extracted with chloroform to provide 2.55 g. of an oil. The oil is recrystallized twice from chloroform to yield the product of the Example m.p. 146°–152° C.

EXAMPLE 7

2-(6-Chloro-2-pyridyl)acetic acid, hydrazide

A 4.3 g. portion of 2-chloro-6-hydrazinopyridine (prepared in Example 1) is treated with acetyl chloride by the procedure of Example 2. The reaction mixture is evaporated to dryness and the solid is treated with a saturated aqueous solution of sodium bicarbonate and filtered to yield 5.33 g. of crude product. The material is recrystallized from acetone to yield 3.70 g. of the product of the Example m.p. 220°–225° C.

EXAMPLE 8

3-(6-Chloro-2-pyridyl)carbazic acid, ethyl ester

A mixture of 3.75 g. of 2-chloro-6-hydrazinopyridine (prepared in Example 1), 50 ml. of pyridine and 3.5 g. of ethyl chloroformate is reacted by the procedure of Example 2. The reaction mixture at room temperature is poured into water and filtered to yield 5.25 g. of crude product. The material is recrystallized from methylene chloride-hexane after filtering through magnesol to yield 4.13 g. of the product of the Example m.p. 139°–141° C.

EXAMPLE 9

2-(6-Chloro-2-pyridyl)difluoroacetic acid, hydrazide

A mixture of 2.5 g. of 2-chloro-6-hydrazinopyridine (prepared in Example 1), 3.5 g. of ethyl difluoroacetate and 40 ml. of absolute ethanol is heated at reflux overnight. The solvent is removed in vacuo to give a white solid. The solid is recrystallized twice from chloroform to yield 1.6 g of the product of the Example m.p. 165°–167° C.

EXAMPLE 10

2-(6-Chloro-2-pyridyl)chloroacetic acid, hydrazide

A mixture of 3.0 g. of 2-chloro-6-hydrazinopyridine (prepared in Example 1), 1.7 g. of pyridine and 35 ml. of methylene chloride is treated with 2.5 g. of chloroacetyl chloride according to the procedure of Example 2. The reaction mixture is stirred for one hour, then is filtered and washed with methylene chloride to collect 2.3 g. of colorless solid. The solid is recrystallized from tetrahydrofuran-hexane to give the product of the Example m.p. 176°–177° C.

EXAMPLE 11

2-(6-Chloro-2-pyridyl)-2-bromopropionic acid, hydrazide

A mixture of 2.1 g. of 2-chloro-6-hydrazinopyridine (prepared in Example 1), 1.25 g. of pyridine and 50 ml. of methylene chloride is cooled to 10° C. and is treated with 2.75 g. of 2-bromopropionyl chloride in 5 ml. of methylene chloride according to the procedure of Example 2. After a heavy precipitate forms the ice bath is removed and the reaction mixture is stirred at room temperature for ½ hour. The precipitate is collected and washed with methylene chloride to provide 2.6 g. of the product of the Example as a colorless solid m.p. 184° C.

EXAMPLE 12

2-(6-Chloro-2-pyridyl)-2-bromoacetic acid, hydrazide

A mixture of 4.0 g. of 2-chloro-6-hydrazinopyridine (prepared in Example 1), 2.4 g. of pyridine and 70 ml. of methylene chloride is treated with 5.8 g. of bromoacetylbromide in 10 ml. of methylene chloride according to the procedure of Example 2. After the addition is completed the reaction mixture is stirred for ½ hour at room temperature and is filtered to collect a white solid. The solid is washed with methylene chloride then is recrystallized from tetrahydrofuran-hexane to yield 3.4 g. of the product of the Example as a colorless solid m.p. 175° C. (d).

I claim:
1. The compound according to the formula:

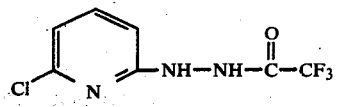

trifluoroacetic acid 2-(6-chloro-2-pyridinyl)hydrazide.
2. The compound according to the formula:

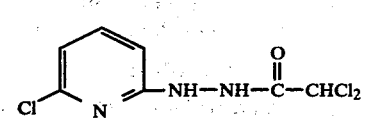

dichloroacetic acid 2-(6-chloro-2-pyridinyl)hydrazide.
3. The compound according to the formula:

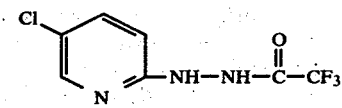

trifluoroacetic acid 2-(5-chloro-2-pyridinyl)hydrazide.
4. The compound according to the formula:

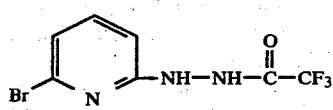

trifluoroacetic acid 2-(6-bromo-2-pyridinyl)hydrazide.
5. The compound according to the formula:

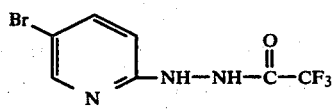

trifluoroacetic acid 2-(5-bromo-2-pyridinyl)hydrazide.
6. The compound according to the formula:

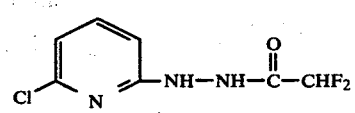

difluoroacetic acid 2-(6-chloro-2-pyridinyl)hydrazide.
7. The compound according to the formula:

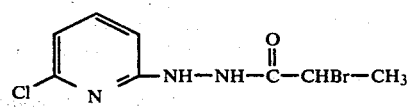

2-bromopropanoic acid 2-(6-chloro-2-pyridinyl)hydrazide.

* * * * *